(12) United States Patent  
Felton

(10) Patent No.: US 12,208,010 B2  
(45) Date of Patent: Jan. 28, 2025

(54) TEMPORARY SPACE-FILLING PENILE IMPLANT FOR CORPORAL HEALING AND NEOPHALLUS CONDITIONING

(71) Applicant: Boston Scientific Scimed, Inc., Maple Grove, MN (US)

(72) Inventor: Jessica Elizabeth Felton, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1102 days.

(21) Appl. No.: 16/947,476

(22) Filed: Aug. 3, 2020

(65) Prior Publication Data

US 2021/0038392 A1 Feb. 11, 2021

Related U.S. Application Data

(60) Provisional application No. 62/883,206, filed on Aug. 6, 2019.

(51) Int. Cl.
| | |
|---|---|
| *A61F 2/26* | (2006.01) |
| *A61F 2/00* | (2006.01) |
| *A61L 27/24* | (2006.01) |
| *A61L 27/32* | (2006.01) |
| *A61L 27/34* | (2006.01) |

(Continued)

(52) U.S. Cl.
CPC ............. *A61F 2/26* (2013.01); *A61F 2/0077* (2013.01); *A61L 27/24* (2013.01); *A61L 27/32* (2013.01); *A61L 27/34* (2013.01); *A61L 27/3608* (2013.01); *A61L 27/3625* (2013.01); *A61L 27/56* (2013.01); *A61L 27/58* (2013.01); *A61F 2210/0004* (2013.01); *A61F 2250/0059* (2013.01); *A61L 2430/34* (2013.01)

(58) Field of Classification Search
CPC .......... A61F 2/26; A61F 2/0077; A61L 27/32; A61L 27/34; A61L 27/3608; A61L 27/3625; A61L 27/56
See application file for complete search history.

(56) References Cited

U.S. PATENT DOCUMENTS 4,335,714 A * 6/1982 Edgerton .................. A61F 2/26
                                                                    600/40
4,545,081 A * 10/1985 Nestor ...................... A61F 2/26
                                                                    623/14.13

(Continued)

FOREIGN PATENT DOCUMENTS

WO     2010068467 A1    6/2010

OTHER PUBLICATIONS

International Search Report and Written Opinion for International Application No. PCT/US2020/070358, mailed Nov. 27, 2020, 13 pages.

*Primary Examiner* — Samuel G Gilbert  
(74) *Attorney, Agent, or Firm* — Brake Hughes Bellermann LLP

(57) ABSTRACT

A temporary space-filling penile implant device for penile surgery includes a body portion, an end portion attached to the body portion, and a cover surrounding the end portion and at least a portion of the body portion. The temporary space-filling penile implant may be configured for insertion into either corpora cavernosa of a penis or into interior tissue of a neophallus, during an inter-procedure time period that occurs between two surgical procedures performed on the penis or the neophallus.

17 Claims, 6 Drawing Sheets

(51) Int. Cl.
*A61L 27/36* (2006.01)
*A61L 27/56* (2006.01)
*A61L 27/58* (2006.01)

(56) References Cited

U.S. PATENT DOCUMENTS

| | | | |
|---|---|---|---|
| 4,589,405 A * | 5/1986 | Hemmeter | A61L 27/00 |
| | | | 600/40 |
| 4,594,998 A * | 6/1986 | Porter | A61F 2/26 |
| | | | 600/40 |
| 9,839,718 B1 | 12/2017 | Carrion et al. | |
| 10,517,730 B1 * | 12/2019 | Loria | A61F 2/26 |
| 2004/0059416 A1 * | 3/2004 | Murray | A61L 27/52 |
| | | | 623/13.15 |
| 2013/0072896 A1 * | 3/2013 | Faccioli | A61F 2/36 |
| | | | 604/93.01 |
| 2018/0098854 A1 | 4/2018 | Allen et al. | |

* cited by examiner

400

TEMPORARY SPACE-FILLING PENILE IMPLANT FOR CORPORAL HEALING AND NEOPHALLUS CONDITIONING

CROSS-REFERENCE TO RELATED APPLICATION

This application is a non-provisional of, and claims priority to, U.S. Patent Application No. 62/883,206, filed on Aug. 6, 2019, entitled "TEMPORARY SPACE-FILLING PENILE IMPLANT FOR CORPORAL HEALING AND NEOPHALLUS CONDITIONING", which is incorporated by reference herein in its entirety.

TECHNICAL FIELD

This disclosure relates generally to penile implants.

BACKGROUND

In some examples, penile prostheses have been used for erectile dysfunction. Such penile prostheses have also been used off-label in penile construction or reconstruction cases, such as female to male (FTM) transgender individuals, and natal males with penile reconstruction (e.g., congenital disorders, amputation (penile cancer), trauma, etc.). For example, a patient undergoes a phalloplasty procedure (e.g., single stage or multiple stages) in which a neophallus is surgically constructed from tissue grafts taken from other parts of the body. Since the neophallus is made of skin and does not contain the erectile tissues of a biological penis, the neophallus does not have the ability to achieve erection.

As referenced above, penile prostheses have been developed to enable patients to have intercourse with a partner, and versions of these prostheses have been used in both natal males and FTM individuals. For example, an elongated shaft of a penile prosthesis device may be inserted into a corpora cavernosa of a natal penis, or into a surgically-constructed analog of a corpora cavernosa within a neophallus.

In various surgical scenarios related to the above types of procedures, it is often necessary to perform two related procedures, separated in time by a period of days, weeks, or months. During such inter-procedure time periods, the penile prosthetic may not be implanted (e.g., may have been temporarily removed, or not yet inserted). Within such inter-procedure time periods, natural healing processes of the body often detract from desired clinical outcomes.

For example, during such inter-procedure time periods, it may not be possible, feasible, or desirable to include a desired penile prosthesis within the patient's natal penis, or constructed neophallus. For example, a patient with a previously-implanted penile prosthesis may be subject to an infection, and it may be necessary to remove the previously-implanted penile prosthesis for a time period required to resolve the infection. In other examples, a phalloplasty procedure may be performed in two or more stages, with a recovery period in between during which a penile prosthetic has not yet been implanted.

During such inter-procedure time periods, a corpora cavernosa of a natal penis may experience fibrosis, scarring, and other effects, which may be associated with undesired outcomes including penile shortening, increased susceptibility to future infections, and increased complications in (re)inserting a future penile prosthesis. Similarly, for example, in the context of a neophallus, when it is time to implant a penile prosthesis, a cavity that may have existed during the neophallus creation procedure will be healed closed, and blunt dissection must be carefully performed so as to not destroy any neovasculature that may have formed within the neophallus when attempting to perform a penile prosthesis implantation procedure.

SUMMARY

According to an aspect, a temporary space-filling penile implant device for penile surgery may include a body portion, an end portion attached to the body portion, and a cover surrounding the end portion and at least a portion of the body portion. The temporary space-filling penile implant may be configured for insertion into either corpora cavernosa of a penis or into interior tissue of a neophallus, during an inter-procedure time period that occurs between two surgical procedures performed on the penis or the neophallus.

According to an aspect, a method of implanting a temporary space-filling penile implant device for penile surgery includes implanting the temporary space-filling penile implant device into either corpora cavernosa of a penis or into interior tissue of a neophallus, during an inter-procedure time period that occurs between two surgical procedures performed on the penis or the neophallus. The temporary space-filling penile implant device may include a body portion, an end portion attached to the cylindrical portion, and a cover over the end portion and at least a portion of the body portion.

According to an aspect, a temporary space-filling penile implant device for penile surgery includes a proximal-specific body portion, a distal-specific body portion, and a connector connecting the proximal-specific portion and the distal-specific portion. The temporary space-filling penile implant device for penile surgery may include an end portion attached to the distal-specific portion, and a cover surrounding the end portion and at least a portion of the distal-specific portion. The temporary space-filling penile implant may be configured for insertion into either corpora cavernosa of a penis or into interior tissue of a neophallus, during an inter-procedure time period that occurs between two surgical procedures performed on the penis or the neophallus.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants, and methods of making and/or surgically implanting such bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1A:
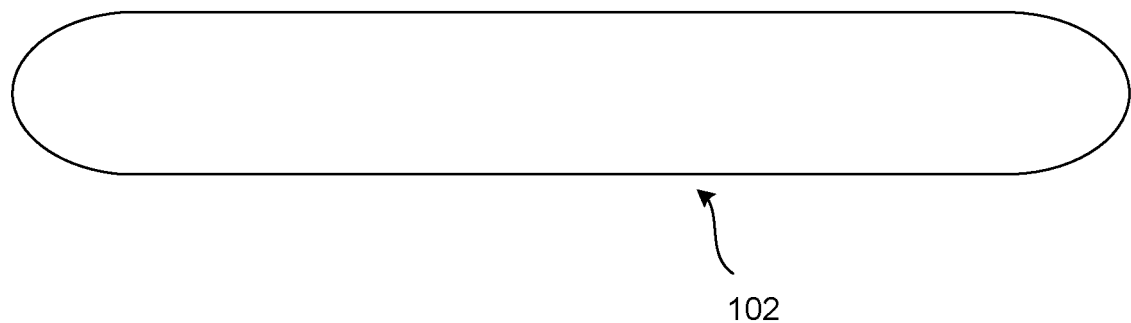
FIG. 1A illustrates a temporary space-filling penile implant for corporal healing and neophallus conditioning, according to an aspect.

FIG. 1A illustrates a temporary space-filling penile implant 102 for corporal healing and neophallus conditioning, according to an aspect. The temporary space-filling penile implant 102 of FIG. 1 may be used during an inter-procedure time period. For example, as described and illustrated below, the temporary space-filling penile implant 102 may be implanted into either a natal penis or a neophallus during an inter-procedure time period, during which the inclusion of the temporary space-filling penile implant 102 provides a number of advantages and benefits, some of which are described below.

In more detailed example scenarios, the temporary space-filling penile implant 102 may be used in the context of erectile dysfunction (ED) procedures, or in the context of neophallus procedures. For example, in the context of ED procedures, it may occur that a patient experiences an infection following implantation of a penile prosthetic for ED.

Historically, typical management when a penile prosthetic (e.g., inflatable penile prosthetic, or IPP) infection is suspected includes antibiotic treatment, removal of all prosthetic components, and a thorough wash out of the retropubic space (or other ectopic reservoir location), scrotum, and corpora cavernosa. Attempted reimplantation may then be considered several months later, when the patient is rendered infection-free.

Unfortunately, removal of the penile prosthetic device will typically lead to fibrosis and scarring of the corporal bodies secondary to the inflammatory process involved. This fibrotic reaction results in penile shortening and makes subsequent insertion of a second IPP more challenging and prone to future infections and other complications. Patient satisfaction after reimplantation, while still high, is noticeably lower after such complications. The options to achieve erection other than another implant are virtually non-existent.

With a prosthetic infection or erosion, classic management has included removal of all hardware with thorough irrigation of the infected spaces. To prevent corporal fibrosis and scarring that can make a subsequent implant challenging, an immediate salvage procedure with a three-piece prosthesis has been advocated when possible. Despite the reported success with immediate salvage Mulcahy washout procedures, recurrent infections or complications are not uncommon.

Causes of corporal fibrosis include complications from an infected implant such as explantation, priapism, penile trauma, and prolonged use of an intracavernosal injection agent. Implant placement in the setting of corporal fibrosis can be technically challenging. Available strategies include incision or excision of the scar, corporotomies with or without grafting, the use of cavernotomes, or other specialized dilators, implant downsizing, and transcorporeal resection.

Meanwhile, in the context of neophallus procedures, it may be difficult to create or maintain a cavity for inclusion of a desired penile prosthetic device. Specifically, the creation of a penis generally involves the creation of a tube within a tube. The inside tube is the urethra, the structure through which men urinate. The outside tube is the penile shaft. This structure, known as the neophallus (neo—for new), is surgically attached to the pelvis. The urethra of the neophallus is connected to the existing urethra. The blood vessels and nerves are attached to those of the pelvis. The exterior of the neophallus is then sculpted to resemble a penis shaft and head.

As referenced above, the two cylinders of the erectile dysfunction penile prosthesis are intended to be implanted within the corpora cavernosa of the natural penis. However, the tube-within-a-tube neophallus does not have corpora, but instead has a single cavity. This cavity is made up of subcutaneous tissue, which is also known as the hypodermis, from the skin flap which consists of fat and connective tissues that house larger blood vessels and nerves.

When it is time to implant a penile prosthesis, the cavity that existed during the neophallus creation has been healed closed and blunt dissection must be carefully performed so as to not destroy any of the neovasculature.

The temporary space-filling penile implant 102 may be implemented in the context of, for example, either an ED penile prosthetic in a natural penis, or in the context of a neophallus. For example, as may be appreciated from the above description, the temporary space-filling penile implant 102 may be useful in the context of an ED penile prosthetic during an inter-procedure time period between a first procedure in which the ED penile prosthetic is removed, e.g., in order to resolve an infection, and a second procedure in which a new ED penile prosthetic is implanted. Further, the temporary space-filling penile implant 102 may be useful in the context of neophallus creation, during an inter-procedure time period between a first procedure in which the neophallus is created, and a second procedure in which the penile prosthetic is implanted.

Thus, the temporary space-filling penile implant 102 provides a temporary space-filling corporal implant to prevent fibrosis, reduce/heal infections, and maintain an available cavity to allow for easier future implantation of a penile prosthesis. According to some aspects, the temporary space-filling penile implant 102 may include a matrix that may be biodegradable over the course of a healing process (e.g., 4-8 weeks).

Figure 1B:
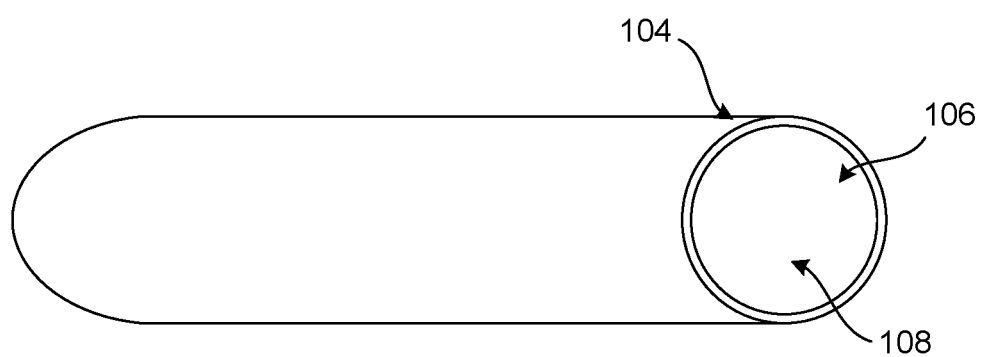
FIG. 1B illustrates an example cross-section of the temporary space-filling penile implant of FIG. 1, according to an aspect.

FIG. 1B illustrates an example cross-section of the temporary space-filling penile implant 102 of FIG. 1A, according to an aspect. In the example of FIG. 1B, the temporary space-filling penile implant 102 may be coated with a hydrophilic or lubricated outer shell or cover 104, for ease of implantation into the corpora cavernosa.

According to some aspects, a matrix 106 of the temporary space-filling penile implant 102 (illustrated in FIG. 1B), or a local drug delivery coating formed on the temporary space-filling penile implant 102, may be impregnated with clinically valuable agents 108. For example, such agents may include anti-fibrotic agents, such as, for example, (cytostatic mitomycin C, 5-fluorouracil, and paclitaxel). Additionally, or alternatively, such agents may include anti-microbial agents.

For a matrix 106 that is not biodegradable, the temporary space-filling penile implant 102 may be removed at the time of penile prosthesis implantation. The materials in the examples above, and similar materials, are flexible to allow for a natural looking flaccid state, and to accommodate a variety of anatomy.

Figure 2:
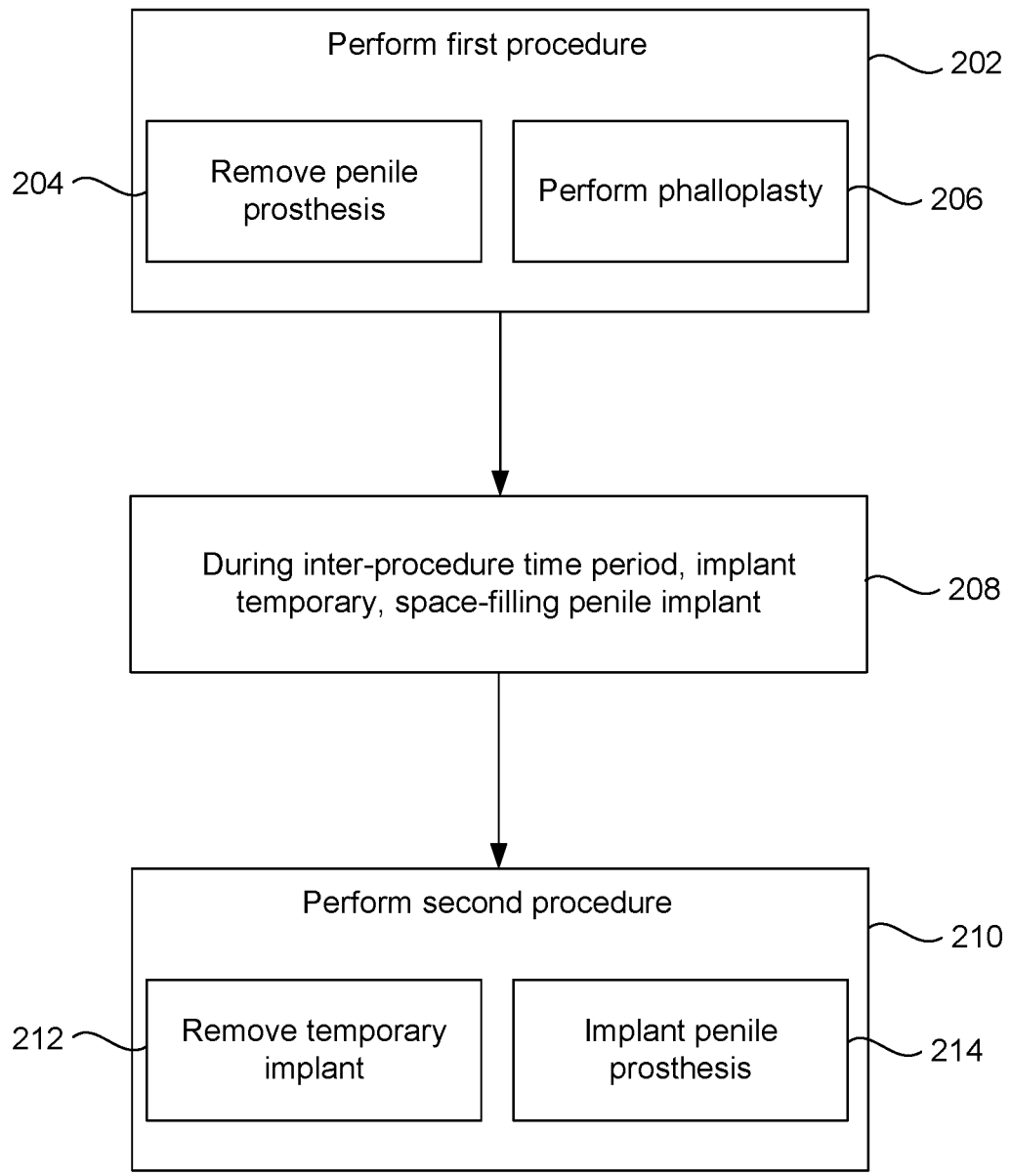
FIG. 2 is a flowchart illustrating an example method using the temporary space-filling penile implant of FIGS. 1A and 1B.

FIG. 2 is a flowchart illustrating an example method using the temporary space-filling penile implant of FIGS. 1A and 1B. In FIG. 2, a first procedure is performed (202). For example, the first procedure may include removal of a penile prosthesis (204), such as removing a penile prosthesis previously-implanted within a corpora cavernosa of a natal penis. In another example, the removal of the penile prosthesis may be performed with respect to a neophallus. In some scenarios, the removal may be performed in response to an infection or other complication from an earlier surgical procedure, such as an original implantation of the penile prosthesis.

According to another aspect, the first procedure may include the performing of a phalloplasty (206). For example, as described herein, a neophallus may be provided in a multi-stage procedure in which a neophallus and neourethra are provided in a first procedure, and a penile prosthetic is provided in a second procedure, e.g., to provide time for the patient to heal in between the multiple stages.

During an ensuing inter-procedure time period, a temporary, space-filling penile implant, such as the implant of FIGS. 1A and 1B, may be implanted (208). For example, as described, the temporary, space-filling penile implant 102 may preserve a shape, function, or other condition of the penis or neophallus during the inter-procedure time period. Consequently, for example, the patient may experience healing and recovery during the inter-procedure time period, while minimizing or eliminating associated reductions in the patient's desired outcome(s).

Thus, a second procedure may be performed (210). In some implementations, the temporary, space-filling penile implant 102 may be removed (212), as part of, or prior to, the second procedure. In other implementations, the temporary, space-filling penile implant 102 may be biodegradable, and may not require removal for the second procedure to be conducted. For example, as in the above examples, the second procedure may be a re-implantation of a penile prosthetic for a natal penis, or an implantation (or re-implantation) of a penile prosthetic into a neophallus (212).

In the present description, it will be appreciated that the term procedure(s), including in the context of the term 'inter-procedure time period,' may be understood to occur at least partially in the context of a more comprehensive surgery. That is, multiple procedures may be performed during a single surgery (e.g., while a patient experiences a single period of administered anesthesia).

For example, a neophallus surgery may include multiple procedures, and the inter-procedure time period may occur at least partially within the larger surgery. For example, during a neophallus surgery, a neophallus may be partially or completely attached during multiple procedures, and the temporary, space-filling penile implant 102 may be inserted following an inter-procedure time period that occurs during the overall neophallus surgery. Thus, the terms 'first procedure' and/or 'second procedure' should be understood to each potentially include one or more procedures.

Figure 3:
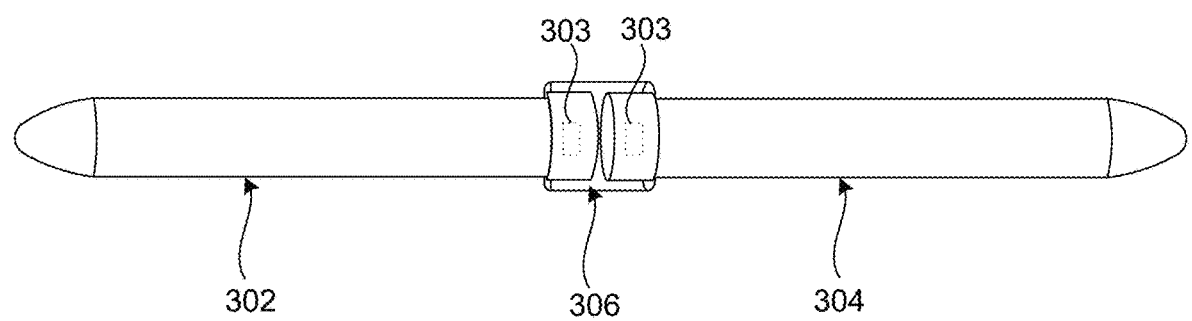
FIG. 3 illustrates an example implementation of the temporary space-filling penile implant of FIG. 1, using proximal-specific and distal specific sections that are connected, according to an aspect.

FIG. 3 illustrates a further example implementation of the temporary space-filling penile implant 102 of FIG. 1. In the example of FIG. 3, proximal-specific section 302 is connected to a distal-specific section 304 using a connector 306.

For example, the temporary space-filling penile implant 102 of FIG. 1 may be trimmable, e.g., to match a patient's anatomy. In the example of FIG. 3, two implementations of the temporary space-filling penile implant 102 may be trimmed, and the two trimmed portions may be used to form the proximal-specific section 302 and the distal-specific section 304.

Example implementations of the example of FIG. 3 provide a number of features and advantages. For example, the proximal-specific section 302 may have a different set of characteristics than the distal-specific section 304. For example, there may be flexibility differences between the proximal-specific section 302 and the distal-specific section 304. By choosing suitable flexibilities, it is possible to provide a more natural appearance, and to choose between a wider range of patient outcomes, to thereby provide highly customized results for each patient. Similarly, other characteristics of the proximal-specific section 302 and the distal-specific section 304 may be selected and optimized, such as size and firmness.

Further, using the proximal-specific section 302 and the distal-specific section 304 may facilitate an ease of implantation of the implementation of FIG. 3, as compared to the implementation of FIG. 1. For example, according to some aspects, the proximal-specific section 302 and the distal-specific section 304 may be implanted separately or sequentially during an implantation procedure, and the connector 306 may be added in conjunction (e.g., in between the sequential implantations), to join the proximal-specific section 302 and the distal-specific section 304 together. Thus, FIG. 3 allows for distal and proximal ends to be implanted independently and trimmed to length, as a one-size fits all approach and for ease of use.

In other implementations, a malleable prosthesis may be used, and bent into a corkscrew shape to be placed. More generally, virtually any suitable shape may be used. For example, a pin may be placed into an end of each tube, with a center section that stops the travel of the pin too far into one end or the other. In addition, the pins could have barbs on the ends to hold them in place.

Couplers may be made of any suitable biocompatible materials, including, e.g., titanium or plastics. One piece, for example the proximal piece, may have a coupler built-in, and only the distal portion may be trimmed to length and fitted with the proximal end. Another version of the outer coupler may have backwards facing teeth 303 on the inside ring that hook into the outer portion of the distal and proximal ends, securing them in place. In still other implementations, without using a coupler or a one-size fits all approach, the proximal and distal portions may mate directly to each other. This could be done using multiple connection types, including, e.g., press-fit/snap-fit, ball and socket, threaded, or tongue and groove.

The proximal-specific section 302 may be an anchoring piece for the neophallus use case. For example, the proximal piece 302 may remain in place for a new prosthetic to mate to. In other implementations, the proximal anchoring may be temporary, and may be removed entirely at a time of a final prosthetic implant. For example, the proximal end may either be a different shape (e.g., a larger, flatter back portion), or may have extension arms that connect to the pelvis. Such a flat portion or the arms may have tissue barbs that hook in to the periosteum (a thin but strong layer of tissue on the outside of bones).

If the anchoring of the proximal section is temporary, it may also have an expected degradable aspect. For example, if the connection was a tissue adhesive, the bond may break down after a suitable period, e.g., approximately six weeks. Biodegradable sutures, or sutures that are intended to be removed by the physician at a later date, may also be used.

Thus, the implementations of FIGS. 1-3 may be used to benefit ED patients and other male patients with a suitable degree of natal penile anatomy. For example, the temporary space-filling penile implant 102 of FIG. 1, or variations thereof, may be used to reduce corporal fibrosis and scarring during an inter-procedure time period during which, e.g., an infection of the patient is resolved.

Further, in other examples, the temporary space-filling penile implant 102 enables relatively easier re-implantation of a full three-piece penile prosthesis at a later time (e.g., at a time of a second, subsequent procedure that follows the inter-procedure time period). For example, the temporary space-filling penile implant 102 serves to retain a shape of corpora cavernosa during an inter-procedure time period that may occur between a penile prosthesis removal and re-implantation. In conjunction, a patient will experience a shorter required operative time, in comparison to placement of a traditional three-piece prosthetic. Still further, a patient will be less prone to future infections, and other complications, as compared to existing techniques.

As referenced above, in addition to the use of the temporary space-filling penile implant 102 in the context of ED patients and other natal males, the temporary space-filling penile implant 102 may be used in the construction and implantation of a neophallus, such as may be used for FTM individuals, or for natal males undergoing penile construction or reconstruction.

Figure 4:
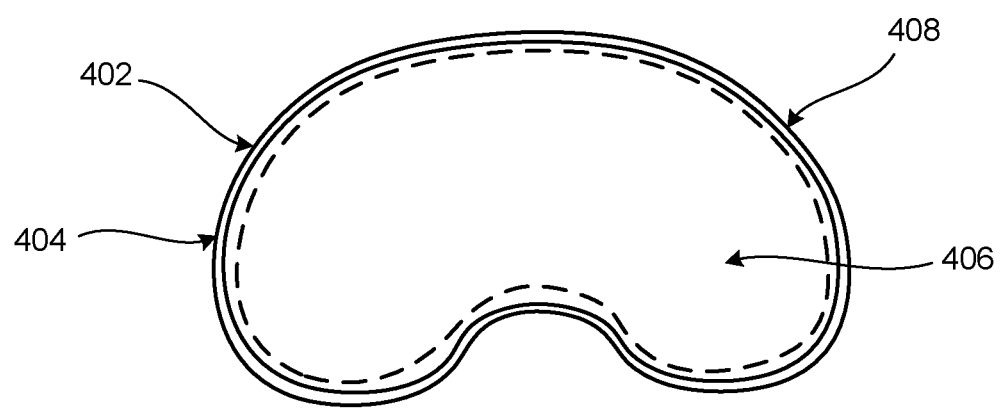
FIG. 4 illustrates a cross section of an example implementation of the temporary space-filling penile implant of FIG. 1, for use in a neophallus, according to an aspect.

Specifically, FIG. 4 illustrates a cross-section of an example implementation of the temporary space-filling penile implant of FIG. 1, for use in a neophallus, according to an aspect. In the example of FIG. 4, a temporary space-filling penile implant 400 includes an outer coating or other covering 402. For example, the outer covering 402 may include a degradable hydrophilic or lubricated outer shell. As described with respect to the outer shell 202 of FIG. 2, such a shell may facilitate and enhance an ease of implantation of the temporary space-filling penile implant 400.

Also similar to FIGS. 1 and 2, a clinically valuable agent 404 may be implanted into one or more materials of the temporary space-filling penile implant 400. For example, the outer covering 402 may represent, or include, an impregnated drug deliver coating with an antimicrobial agent.

Additionally, or alternatively, such an agent may be implanted within a matrix 406 making up an interior of the temporary space-filling penile implant 400. As described with respect to FIG. 2, according to some aspects, such a matrix may be biodegradable over the course of a healing process (e.g., 4-8 weeks) that occurs during an inter-procedure time period. According to other aspects, the matrix 406 may not be degradable, and may be removed following an ending of the inter-procedure time period, e.g., in conjunction with performing a second procedure that follows the inter-procedure time period (including implantation of a penile prosthesis device).

A tissue ingrowth layer 408 may be included that, e.g., surrounds the matrix 406. More specifically, the tissue ingrowth cover 408 provides a structure that is located between the matrix 406 and an interior wall of a neophallus (as illustrated explicitly in FIG. 5). For example, the tissue ingrowth cover 408 may be useful in simulating characteristics and aspects of natural penile function, fills a void between the matrix 406 and an interior wall of the neophallus, acts as a bulking agent, and otherwise contributes to successful and satisfactory patient outcomes when the temporary space-filling penile implant 400 is required during an inter-procedure time period.

In some examples, the tissue ingrowth cover 408 includes tissue ingrowth materials, such as hydroxyapatite. In some examples, the tissue ingrowth cover 408 includes, or uses, cadaveric bone, animal biologic tissues, and materials known for tissue ingrowth properties. In additional or alternative implementations, porous, hydroxyapatite-type material for bone/tissue ingrowth, may be used, and/or preformed open cell foam matrix for tissue ingrowth. In further additional or alternative implementations, the tissue ingrowth cover 408 may include suitable textile(s), such as woven fabric or knit mesh. The tissue ingrowth cover 408 may include, or use, porous plastic materials, such as ePTFE. The types of animal biologic materials referenced above may include, in some examples, one or more of collagen, bovine pericardium, or porcine dermis. The tissue ingrowth cover 408 may also be embedded or impregnated with substances that are anti-microbial, improve tissue ingrowth, and/or promote healing, similar to the agent(s) 404.

The tissue ingrowth cover 408 may serve to prevent erosion, while providing improved structural integrity to the neophallus. The tissue ingrowth cover 408 may further serve to improve an aesthetic appearance (e.g., additional girth) of the neophallus, as well as providing improved palpability (e.g., more natural feel).

Figure 5:
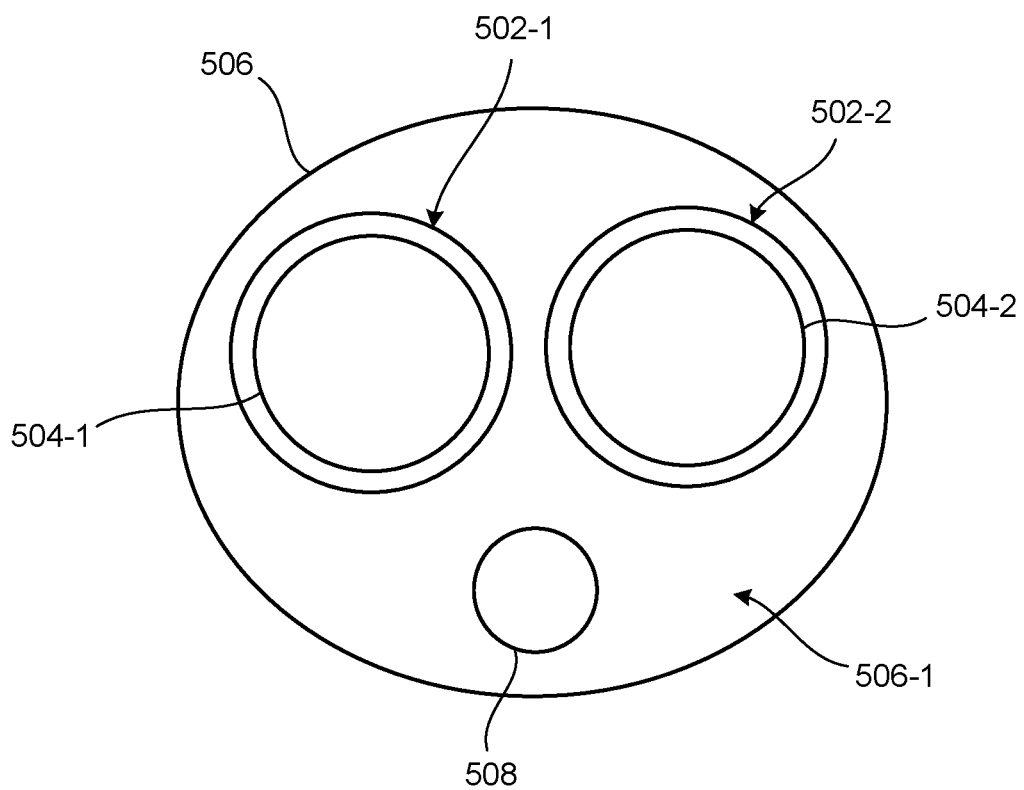
FIG. 5 illustrates a cross section of a neophallus with the temporary space-filling penile implant of FIG. 1 implanted therein, according to an aspect.

The tissue ingrowth cover 408 helps to form a capsule, and may perform a function similar to the tunica albuginea in natal male corpora cavernosa, as described in more detail with respect to FIG. 5. The temporary space-filling penile implant 400 may be biodegradable so that all that remains during the future penile implant procedure is the ingrown tissue capsule, or, in other implementations, the temporary space-filling penile implant 400 may not be degradable. In such cases, as referenced above, the temporary space-filling penile implant 400 may be removed, or may be left in the neophallus to provide additional bulk to the neophallus. Although the temporary space-filling penile implant 400 would not be suitable for penetrative sex, the additional bulk provided by the implant would create a more natural looking phallus.

In the example of FIG. 4, the temporary space-filling penile implant 400 is illustrated as having a kidney bean type cross-section that is specialized for the neophallus. In general, providing the temporary space-filling penile implant 400 with a cross-section that is kidney bean, or crescent, horseshoe, or otherwise suitably curved to accommodate a neourethra, may be advantageous. However, as illustrated in the example of FIG. 5, the temporary space-filling penile implant 400 may be formed in other shapes when used in neophallus, including a circular shape.

As referenced in, and appreciated from, the above description, the temporary space-filling penile implant 400 provides a number of benefits to a neophallus patient. For example, the temporary space-filling penile implant 400 adds bulk to a neophallus to look more like natural phallus (improved aesthetics). The temporary space-filling penile implant 400 minimizes chances of future penile implant erosion, and provides a reduction in neophallus healing time and in neophallus infection. The temporary space-filling penile implant 400 provides improved structural integrity to the neophallus, as well as improved palpability (e.g., more natural feel). The tissue ingrowth cover 408 also may provide an anchoring function in anchoring the neophallus to a pelvic region of the patient, in a standardized, consistent, fast, efficient manner, that avoids or minimizes a need for specialized anchoring procedures by a surgeon during an attachment procedure.

FIG. 5 illustrates a cross section of a neophallus 506 with the temporary space-filling penile implant of FIG. 1 implanted therein, according to an aspect. The example of FIG. 5 illustrates a dual-cylinder implementation of the temporary space-filling penile implant of FIG. 1 implanted within the neophallus 506, consistent with FIG. 6, below, and designed to more closely mimic natural penile anatomy.

Specifically, FIG. 5 illustrates a cross-section of a neophallus 506 showing a temporary space-filling penile implant 504-1 and a temporary space-filling penile implant 504-2, and with a neourethra 508. The temporary space-filling penile implant 504-1 is covered in the cross section with a corresponding cover 502-1, while the temporary space-filling penile implant 504-2 is covered in the cross section with a corresponding cover 502-2. For example, the covers 502-1 and 502-2 may correspond to the cover 202 of FIG. 2, or the cover 402 and/or the tissue ingrowth cover 408 of FIG. 4.

Such a dual-cylinder approach may be desirable in the context of a neophallus, because this approach more closely mimics natural male anatomy, which includes two corpora of the corpora cavernosa. Natural penile anatomy also includes corpus spongiosum, tunica albuginea, and other erectile tissues, structures, or aspects.

Figure 6:
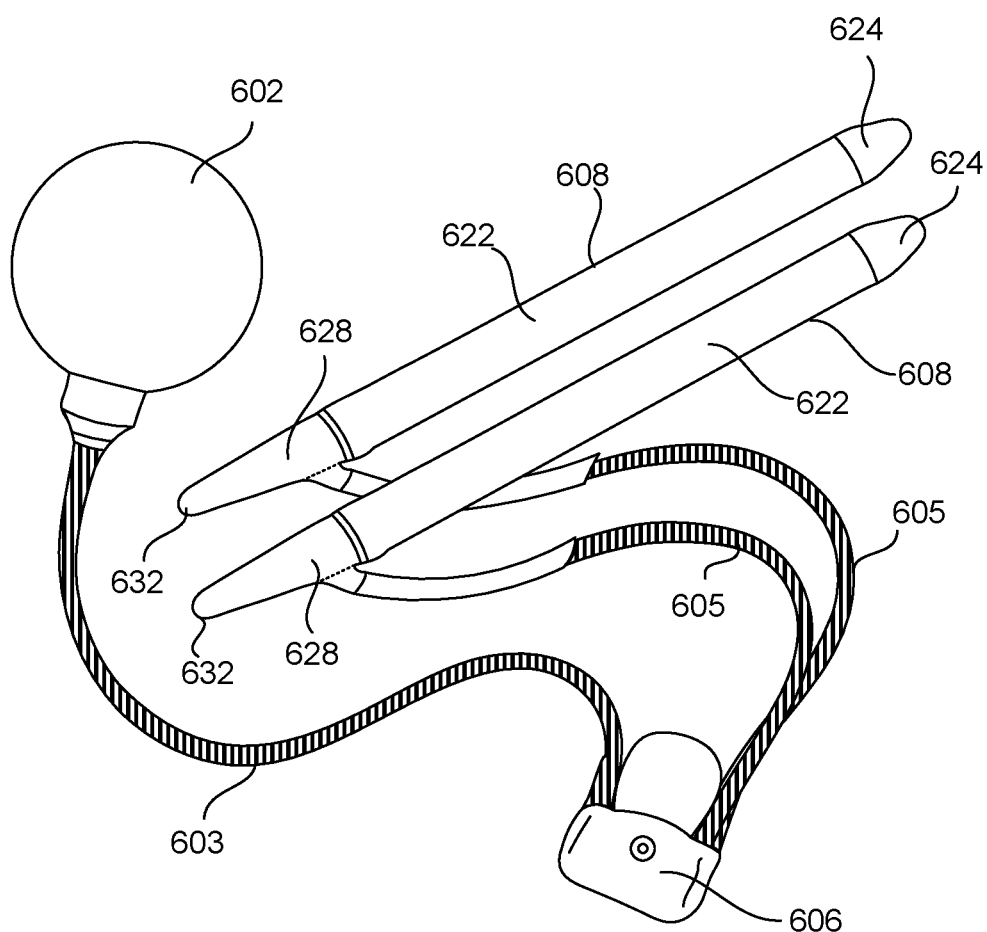
FIG. 6 illustrates a penile prosthesis device, according to an aspect.

However, the neophallus 506 typically includes a rolled skin flap(s) with an interior 506-1 that, includes, e.g., fat and connective tissues. As a result, if a dual-cylinder approach is attempted in the context of conventional neophallus surgery, the two cylinders are prone to crossing and/or migration, when inflated or deflated, which may lead to malfunctions and other undesirable outcomes. Therefore, conventional approaches to neophallus surgery with penile prostheses often include only a single cylinder, including, if necessary, removal of one of two cylinders that may be included in a manufactured penile prosthetic system (such as shown in FIG. 6). Such single cylinder approaches may result in undesired or suboptimal characteristics of the resulting neophallus, including, e.g., with respect to size and rigidity of the resulting neophallus.

As may be understood from the present description, and from the illustration of FIG. 5, inclusion of temporary space-filling penile implants 504-1 and 504-2 during an inter-procedure time period enables maintenance of an opening(s) for implantation of both cylinders of a dual-cylinder penile prosthetic device (as in FIG. 6), as well as all of the other various features and advantages of the temporary space-filling penile implants 504-1 and 504-2 described herein.

Further, as also referenced above, if the covers 502-1 and 502-2 include tissue ingrowth covers as described above with respect to FIG. 4, then such tissue ingrowth covers 502-1 and 502-2 may provide functions similar to a tunica albuginea in a natural penis. For example, the tunica albuginea refers to a fibrous layer of connective tissue that surrounds and supports the corpora cavernosa of the penis. In FIG. 5, the tissue ingrowth covers 502-1 and 502-2 surround and support the dual cylinders 504-1 and 504-2 of the temporary space-filling penile implants, and prevent crossover and migration of the cylinders 504-1 and 504-2.

Thus, the example embodiment of FIG. 5 is able to provide the advantages of a dual-cylinder approach, as referenced above.

FIG. 6 illustrates a penile prosthesis device, according to an aspect. In the example of FIG. 6, the penile prosthesis device 600 may be an inflatable penile prosthesis device. The inflatable penile prosthesis 600 may be an example of any of the implantable devices discussed herein as being implanted into a natal penis or neophallus, and may enable or enhance many of the features discussed with reference to the previous figures.

The penile prosthesis device 600 may include a pair of cylinders 608, and the pair of cylinders or inflatable members 608 are configured to be implanted in a pelvic region. For example, one or both of the cylinders 608 may be coupled to a suitable anchor plate. The cylinder 608 may include a first end portion 624, a cavity or inflation chamber 622, and a second end portion 628 having a rear tip 632.

A pump assembly 606 may be implanted into the patient's scrotum. A pair of conduit connectors 605 may attach the pump assembly 606 to the pair of inflatable members or cylinders 608 such that the pump assembly 606 is in fluid communication with the pair of inflatable members or cylinders 608. Also, the pump assembly 606 may be in fluid communication with the fluid reservoir 602 via a conduit connector 603. The fluid reservoir 602 may be implanted into the patient's abdomen. The inflation chamber or portion 622 of the cylinder 608 may be disposed within the neophallus. The first end portion 624 of the cylinder 608 may be at least partially disposed within the glans portion of the neophallus. The second end portion 628 may be implanted into the patient's pubic region with the rear tip 632 configured to be attached to an anchor plate or other suitable connecting member(s).

The patient may operate the pump assembly 606 to start an inflation mode, where the pump assembly 606 is configured to facilitate the transfer of fluid from the fluid reservoir 602 to the cylinders 608. In some examples, when the user switches to the deflation mode, at least some of the fluid can automatically be transferred back to the fluid reservoir 602 (due to the difference in pressure from the cylinders 608 to the fluid reservoir 602).

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A method comprising:
   performing a first surgical procedure including:
      removing a first penile prosthesis,
      implanting a first portion of a temporary space-filling penile implant device into either corpora cavernosa of a penis or into interior tissue of a neophallus, and
      implanting a second portion of the temporary space-filling penile implant device; and coupling the first portion of the temporary space-filling penile implant device to the second portion of the temporary space-filling penile implant device after at least one of the first portion of the space-filling penile implant device and the second portion of the space-filling implant device has been implanted, wherein the temporary space-filling penile implant device includes a cover over at least a portion of the space-filling penile implant device; and
   performing a second surgical procedure including:

removing the space-filling penile implant device, and implanting a second penile prosthesis.

2. The method of claim 1, wherein the first portion of the temporary space filling penile implant device includes a biodegradable matrix.

3. The method of claim 1, wherein at least one of the first portion of the temporary space-filling penile implant and the second portion of the temporary space-filling penile implant has a crescent shape.

4. The method of claim 1, wherein the temporary space-filling penile implant device includes a proximal-specific portion and a distal-specific portion.

5. The method of claim 1, wherein the cover includes a tissue ingrowth cover.

6. The method of claim 5, wherein the tissue ingrowth cover is formed using one or more of: hydroxyapatite, porous plastic, animal biologic tissues, a textile, and a pre-formed open cell foam matrix.

7. The method of claim 5, wherein the at least one tissue ingrowth cover is formed using one or more animal biologic tissues including one or more of: cadaveric bone, collagen, bovine pericardium, or porcine dermis.

8. A temporary space-filling penile implant device for penile surgery, the temporary space-filling penile implant device comprising:
a body portion, the body portion including a proximal specific portion and a distal specific portion configured to be coupled to the proximal specific portion after at least one of the proximal specific portion and the distal specific portion have been implanted in a body of a patient, the proximal specific portion being coupled to the distal specific portion via a coupler having teeth configured to engage at least one of the proximal specific portion and the distal specific portion;
an end portion attached to the body portion; and
a cover surrounding the end portion and at least a portion of the body portion,
wherein the temporary space-filling penile implant is configured for insertion into either corpora cavernosa of a penis or into interior tissue of a neophallus, during an inter-procedure time period that occurs between two surgical procedures performed on the penis or the neophallus.

9. The temporary space-filling penile implant device of claim 8, wherein the body portion comprises a biodegradable matrix.

10. The temporary space-filling penile implant device of claim 8, wherein the proximal-specific portion has a first degree of flexibility, and the distal-specific portion has a second degree of flexibility.

11. The temporary space-filling penile implant device of claim 8, wherein the proximal-specific portion and the distal-specific portion are joined by a connector.

12. The temporary space-filling penile implant device of claim 8, wherein the end portion includes a proximal tip configured to facilitate anchoring to a pelvic region.

13. The temporary space-filling penile implant device of claim 8, wherein the cover includes a tissue ingrowth cover.

14. The temporary space-filling penile implant device of claim 13, wherein the tissue ingrowth cover is formed using one or more of: hydroxyapatite, porous plastic, animal biologic tissues, a textile, a pre-formed open cell foam matrix, or one or more animal biologic tissues.

15. A temporary space-filling penile implant device for penile surgery, the temporary space-filling penile implant device comprising:
a proximal-specific body portion;
a distal-specific body portion;
a connector connecting the proximal-specific portion and the distal-specific body portion and configured to be coupled to the proximal-specific body portion and to the distal-specific body portion after at least one of the proximal-specific body portion and the distal-specific body portion has been implanted in a body of a patient, the connector having teeth configured to engage at least one of the distal-specific body portion and the proximal-specific body portion;
an end portion attached to the distal-specific portion; and
a cover surrounding the end portion and at least a portion of the distal-specific portion,
wherein the temporary space-filling penile implant is configured for insertion into either corpora cavernosa of a penis or into interior tissue of a neophallus, during an inter-procedure time period that occurs between two surgical procedures performed on the penis or the neophallus.

16. The temporary space-filling penile implant device of claim 15, wherein the proximal-specific body portion has a first degree of flexibility and the distal-specific body portion has a second degree of flexibility.

17. The temporary space-filling penile implant device of claim 15, wherein the cover includes a tissue ingrowth cover.

* * * * *